United States Patent [19]

Collington et al.

[11] Patent Number: 4,847,369

[45] Date of Patent: Jul. 11, 1989

[54] CYCLOPENTYL ETHERS AND THEIR PREPARATION AND PHARMACEUTICAL FORMULATION

[75] Inventors: Eric W. Collington, Knebworth; Harry Finch, Letchworth; Duncan B. Judd; James D. Meadows, both of Ware, all of England

[73] Assignee: Glaxo Group Limited, London, England

[21] Appl. No.: 110,777

[22] Filed: Oct. 21, 1987

[30] Foreign Application Priority Data

Oct. 22, 1986 [GB] United Kingdom ............... 8625323
Oct. 22, 1986 [GB] United Kingdom ............... 86258324

[51] Int. Cl.$^4$ .................. C08B 30/18; C08B 37/16; A61K 31/557
[52] U.S. Cl. .................. 536/46; 536/103; 514/212; 514/613; 514/708; 514/60; 560/53; 568/367
[58] Field of Search ............ 536/46, 103; 514/212, 514/613, 708, 60; 560/53, 379; 568/367

[56] References Cited

U.S. PATENT DOCUMENTS

| 4,265,891 | 5/1981 | Collington et al. | 514/212 |
| 4,438,111 | 3/1984 | Collington et al. | 514/212 |
| 4,438,112 | 3/1984 | Collington et al. | 514/212 |

FOREIGN PATENT DOCUMENTS

| 62-129218A | 6/1987 | Japan | 31/557 |
| 2174702 | 11/1986 | United Kingdom . | |

*Primary Examiner*—Ronald W. Griffin
*Attorney, Agent, or Firm*—Bernard, Rothwell & Brown

[57] ABSTRACT

Compounds are described of formula (1)

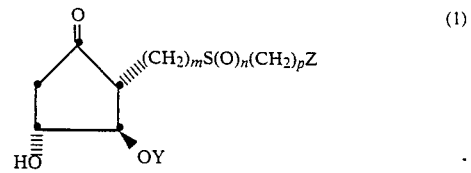

wherein
m is 1 to 4;
n is zero, 1 or 2;
p is 1 to 4;
Z is a group $CO_2R^1$ where $R^1$ is
  (a) a hydrogen atom or an alkyl, phenalkyl or 2-naphthyl group;
  (b) phenyl or substituted phenyl;
  (c) $-CH_2COR^5$ where $R^5$ is phenyl substituted phenyl or 2-naphthyl;
or Z is $-CH_2OH$, $-CHO$ or $CONHR^9$ [where $R^9$ is a hydrogen atom or alkyl, aryl, $-COR^{10}$ (where $R^{10}$ is a hydrogen atom or an alkyl or aryl group) Or $-SO_2R^{11}$ (where $R^{11}$ is an alkyl or aryl group)];
Y is substituted or unsubstituted 3-phenoxy-2-hydroxy-propyl.

These compounds inhibit gastric acid secretion and provide gastrointestinal cytoprotection, and may be formulated for use in the treatment of ulcers.

10 Claims, No Drawings

CYCLOPENTYL ETHERS AND THEIR PREPARATION AND PHARMACEUTICAL FORMULATION

Prostaglandin $E_2$ is a naturally occurring substance which has many physiological actions. For example, it inhibits gastric acid secretion and provides gastrointestinal cytoprotection, lowers blood pressure, stimulates and relaxes smooth muscle, inhibits platelet aggregation and inhibits lipolysis.

Synthetic $PGE_2$ analogues offer the possibility of different potency, longer duration of activity and increased selectivity of action and are therefore of considerable interest.

We have now found a new group of cyclopentyl ethers that have $PGE_2$-type activity. Compounds in this class have a particularly useful profile of biological action. In particular they have shown high potency and improved slectivity as regards the inhibition of gastric acid secretion and gastrointestinal cytoprotection and are therefore of interest in the treatment of ulcers. Compounds according to the invention also have a lipid lowering action and are of interest in the treatment of clinical conditions in which the underlying aetiology is associated with lipid imbalance or hyperlipidemia.

The invention thus provides compounds of the general formula (1)

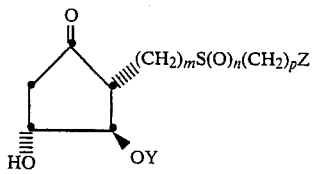

(1)

wherein
m is 1 to 4
n is zero, 1 or 2;
p is 1 to 4;
Z is a group $CO_2R^1$ where $R^1$ is
(a) a hydrogen atom or a $C_{1-6}$ alkyl, $C_{7-10}$ phenalkyl or 2-naphthyl group;
(b) phenyl[optionally substituted by $C_{1-4}$ alkyl, $C_{1-4}$ alkoxy, $C_{1-4}$ alkanoyl, methylthio, methylsulphinyl, methylsulphonyl, halogen, $-CO_2R^2$ (where $R^2$ is a hydrogen atom or $C_{1-4}$ alkyl or phenyl), $-NHCOR^2$ (where $R^2$ is as defined above or is a phenyl group optionally substituted by hydroxyl, $CH_3CONH-$ or

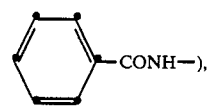

-CONR$^3$R$^4$ (where $R^3$ and $R^4$ may be the same or different and are each a hydrogen atom or a $C_{1-4}$ alkyl group), $-NHCONH_2$, $-CH_2CH(CONH_2)NHCOCH_3$ or

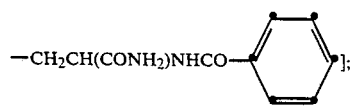

(c) a group $-CH_2COR^5$ where $R^5$ is phenyl [optionally substituted by $C_{1-4}$ alkyl, $C_{1-4}$ alkoxy, $C_{1-4}$ alkanoyl, methylthio, methylsulphinyl, methylsulphonyl, halogen, $-CO_2R^6$ (where $R^6$ is a hydrogen atom or $C_{1-4}$ alkyl or phenyl), $-CONR^7R^8$ (where $R^7$ and $R^8$ may be the same or different and are each a hydrogen atom or a $C_{1-4}$ alkyl group), $-NHCOR^6$ (where $R^6$ is as defined above, or is a phenyl group optionally substituted by hydroxyl, $CH_3CONH-$ or

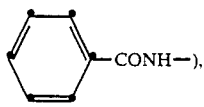

$-NHCONH_2$, $-CH_2CH(CONH_2)NHCOCH_3$ or

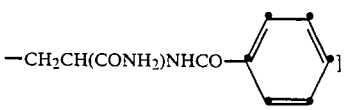

or $R^5$ is 2-naphthyl; or Z is $-CH_2OH$, $-CHO$ or $CONHR^9$ [where $R^9$ is a hydrogen atom or $C_{1-4}$ alkyl, aryl, $-COR^{10}$ (where $R^{10}$ is a hydrogen atom or a $C_{1-4}$ alkyl or aryl group) or $-SO_2R^{11}$ (where $R^{11}$ is a $C_{1-4}$ alkyl or aryl group)];

Y is

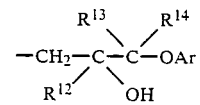

where $R^{12}$, $R^{13}$ and $R^{14}$ are each a hydrogen atom or methyl and at least one is a hydrogen atom, and Ar is a phenyl group (optionally substituted by one or two $C_{1-4}$ alkyl, $C_{1-4}$ alkoxy, $C_{1-4}$ alkylthio, $C_{1-4}$ alkylsulphinyl, $C_{1-4}$ alkylsulphonyl, halogen or trifluoromethyl groups);
and the physiologically acceptable salts, solvates and complexes (e.g. cyclodextrin complexes) thereof.

The structural formula herein are to be understood to include the enantiomers of each of the compounds concerned as well as mixtures of the enantiomers including racemates.

In general, the compounds of formula (1) in which the carbon atom carrying the group $-(CH_2)_m-S(O)_n(CH_2)_pZ$ and/or the carbon atom in the group Y carrying the $-OH$ group are in the R-configuration (particularly the former) and mixtures containing such isomers are preferred.

The term 'alkyl' as a group or part of a group within the definition of the compounds of formula (1) is intended to cover straight or branched chain moieties, and may be, for example, a methyl, ethyl, n-propyl, i-propyl, n-butyl, s-butyl, or t-butyl group. The term 'halogen' meams fluorine, chlorine, bromine or iodine.

The aryl group referred to above in the definition of Z may be, for example, phenyl.

Compounds of formula (1) in which Z is $CO_2H$ or contains a $CO_2H$ grouping can form salts with bases. Examples of such salts are alkali metal (e.g. sodium), alkaline earth metal (e.g. calcium) and amine (e.g. piperazine) salts.

When Z is a group $CO_2R^1$, examples of suitable $R^1$ groups of type (a) are hydrogen, $C_{1-3}$ alkyl, benzyl, phenethyl and 2-naphthyl, and $R^1$ is preferably hydrogen or, more preferably, methyl or 2-naphthyl.

When Z is a group $CO_2R^1$, examples of suitable $R^1$ groups of type (b) are phenyl optionally substituted in the ortho, meta or, in particular, para position by a chlorine or bromine atom or a methyl, ethyl, propyl, n-butyl, t-butyl, methoxy, ethoxy, propoxy, butoxy, acetyl, propionyl, methylthio, methylsulphinyl, methylsulphonyl, $-CO_2H$, $-CO_2CH_3$, $-CO_2CH_2CH_3$,

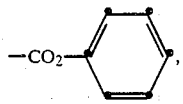

$-NHCHO$, $-NHCOCH_3$, benzoylamino, (acetylamino)benzoylamino, (hydroxy)benzoylamino, $-CONH_2$, $-CONHCH_3$, $-CON(CH_3)_2$, $-CONHCH_2CH_3$, $-CON(CH_2CH_3)_2$, $-NHCONH_2$, $-CH_2CH(CONH_2)NHCONH_3$ or

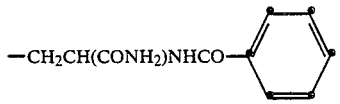

group.

Particularly useful substituents which may be present on the $R^1$ phenyl group include $C_{1-4}$ alkoxy, $C_{1-4}$ alkanoyl, methylthio, methylsulphonyl, $-CO_2R^2$, $-NHCOR_2$, $-CONR^3R^4$ [where $R^2$, $R^3$ and $R^4$ are as defined for formula (1)], $-NHCONH_2$, or $-CH_2CH(CONH_2)NHCOCH_3$. Especially useful substituents of this type include methoxy, acetyl, methylthio, methylsulphonyl, $-CO_2CH_3$, $-NHCOCH_3$, benzoylamino, (p-acetylamino)benzoylamino, (p-hydroxy)benzoylamino, $-CONH_2$, $-CON(CH_3)_2$, $-NHCONH_2$ or $-CH_2CH(CONH_2)NHCOCH_3$.

In general, when $R^1$ is a group of type (b) it is preferably a phenyl group substituted (particularly in the para position) by a methoxy, acetyl, $-CO_2CH_3$, $-NHCOCH_3$, benzoylamino, $-CONH_2$, $-CON(CH_3)_2$ or $-CH_2CH(CONH_2)NHCOCH_3$ group.

When Z is a group $CO_2R^1$, examples of suitable $R^1$ groups of type (c) are $-CH_2COR^5$ where $R^5$ is a phenyl group substituted (particularly in the para position) by a methoxy, acetyl, $-CO_2CH_3$, $-NHCOCH_3$, benzoylamino, $-CONH_2$, $-CON(CH_3)_2$ or $-CH_2CH(CONH_2)NHCOCH_3$ group, or $R^5$ is a 2-naphthyl group. Especially useful substituents of this type include $-NHCOCH_3$, benzoylamino, acetyl or $-CONH_2$ preferably attached at the para position on the phenyl group.

When Z is other than $CO_2R^1$ examples of suitable Z groups are $-CH_2OH$, $-CHO$ or $-CONHR^9$ [where $R^9$ is a hydrogen atom or methyl, ethyl, phenyl, $-COR^{10}$ (where $R^{10}$ is methyl or phenyl) or $-SO_2R^{11}$ (where $R^{11}$ is methyl or phenyl)], and is preferably $-CH_2OH$, $-CHO$, $-CONH_2$, $-CONHCH_3$, $-CONHCOCH_3$, $-CONHSO_2CH_3$ or

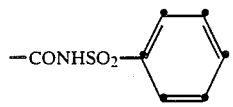

In the group Y, $R^{13}$ and $R^{14}$ are preferably hydrogen atoms.

When the Ar phenyl group is substituted, the substituent may for example be methyl, ethyl, propyl, butyl, methoxy, ethoxy, propoxy, butoxy, methylthio, methylsulphinyl, methylsulphonyl, fluoro, chloro, bromo or trifluoromethyl. Preferably, only a single substituent is present, particularly at the para-position. In general, Ar is preferably phenyl or phenyl substituted by halogen, particularly fluoro or chloro.

In general compounds of formula (1) in which n is zero are preferred.

The preferences indicated above apply both separately and in combination with one or more of the other stated preferences.

A preferred group of compounds of the invention thus has the formula (1) in which:

n is zero
m is 3 or 4 and p is 1 or
m is 2 or 3 and p is 2 or
m is 1 and p is 4 or
m is 2 and p is 3;
Z is a group $CO_2R^1$ [where $R^1$ is a hydrogen atom or $C_{1-3}$ alkyl (particularly methyl), 2-naphthyl or phenyl substituted (preferably in the para position) by methoxy, acetyl, $-CO_2CH_3$, $-NHCOCH_3$, benzoylamino, $-CONH_2$, $-CON(CH_3)_2$ or $-CH_2CH(CONH_2)NHCOCH_3$];
$R^{12}$ is a hydrogen atom or methyl;
$R^{13}$ and $R^{14}$ are hydrogen atoms;
Ar is phenyl or phenyl substituted by fluoro or chloro; including the physiologically acceptable salts, solvates and complexes (e.g. cyclodextrin complexes) thereof.

Compounds of this type in which the carbon atom carrying the $-(CH_2)_mS(O)_n(CH_2)_pZ$ group is in the R-configuration are particularly preferred. Especially preferred compounds of this type are those in which Z is a group $CO_2R^1$ where $R^1$ is a hydrogen atom or, more preferably, methyl or phenyl substituted in the para position by $-CO_2CH_3$ or benzoylamino.

Particularly important compounds of the invention are: [1R-[1α,2β(R*),3α]]-4-(Benzoylamino)phenyl 4-[[2-[3-hydroxy-2-(2-hydroxy-3-phenoxypropoxy)-5-oxocyclopentyl]ethyl]thio]butanoate; [1R-[1α,2β(R*)-,3α]]-Methyl 4-[[[[2-3-hydroxy-2-(2-hydroxy-3-phenoxypropoxy)-5-oxocyclopentyl]ethyl]thio]-1-oxobutyl]oxy]benzoate; and [1R-[1α,2β(R*),3α]]-(−) Methyl 4-[[2-[-3-hydroxy-2-(2-hydroxy-3-phenoxypropoxy)-5-oxocyclopentyl]ethyl]thio]butanoate; and complexes (e.g. cyclodextrin complexes) thereof.

Compounds of formula (1) inhibit gastric secretion, as determined for example by their ability to inhibit histamine-induced secretory repsonses in the rat perfused stomach, following the method of Ghosh and Schild in Br. J. Pharmacol., 1958, 13, 54 as modified by Parsons M. E., Ph. D Thesis, University of London, 1969.

The compounds also provide gastrointestinal cytoprotection, as determined for example by their ability to inhibit ethanol-induced lesions in the conscious rat, following the method of Robert et al in Gastroneterology, 1979, 77, 433, modified by the use of 5 mg/kg/s.c. indomethacin prior to the administration of the test compound.

Compounds of the invention are also able to lower lipid levels as may be demonstrated in standard animal models for example by determining their ability to lower non-esterified fatty acid levels in the starved rat (P. P. Lovisolo et. al., *Pharmacological Research Communications*, 1981, 13, 163–174; E. Schillinger and O. Loge, *Biochemical Pharmacology*, 1974, 23, 2283–2289).

The compounds are thus of interest in the prevention and/or treatment of ulcers. The may also be used in the treatment of other conditions which arise from the hypersecretion of gastric acid. They may also be used for the prevention and/or treatment of conditions in which the underlying aetiology is associated with lipid imbalance or hyperlipidemia.

According to a further aspect of the present invention we therefore provide a compound of formula (1) or a physiologically acceptable salt or complex (eg cyclodextrin complex) thereof for use in the prevention and/or treatment of ulcers and other conditions arising from hypersecretion of gastric acid. We also provide a compound of formula (1) or a physiologically acceptable salt or complex (e.g. cyclodextrin complex) thereof for use in the prevention and/or treatment of conditions in which the underlying aetiology is associated with lipid imbalance or hyperlipidemia.

According to another aspect of the invention we provide a method of treating the human or non-human animal body to combat ulcers and other conditions arising from hypersecretion of gastric acid or conditions in which the underlying aetiology is associated with lipid imbalance or hyperlipidemia, which method comprises administering to the said body an effective amount of a compound of formula (1) or a physiologically acceptable salt or complex (e.g. cyclodextrin complex) thereof.

It will be appreciated that the compounds according to the invention may advantageously be used in conjunction with one or more other therapeutic agents, such as non-steoidal anti-inflammatory agents, or different anti-ulcer agents. It is to be understood that the present invention covers the use of a compound of formula (1) or a physiologically acceptable salt or complex (eg cyclodextrin complex) thereof in combination with one or more other therapeutic agents.

In a further aspect of the present invention we provide a pharmaceutical composition comprising as an active ingredient a compound of formula (1) or a physiologically acceptable salt or complex (eg cyclodextrin complex) thereof together with one or more pharmaceutical carriers or excipients.

Compounds may be formulated in conventional manner with one or more pharmaceutical carriers, for example for oral, buccal, parenteral or rectal administration.

The compounds may be formulated for oral administration as, for example, tablets, capsules, powders, solutions or syrups prepared by conventional means with acceptable excipients.

The compounds may be formulated for parenteral administration by bolus injections or continuous infusion. Formulations for injections may be presented in unit dosage form in ampoules, or in multi-dose containers, with an added preservative.

For buccal administration, the compounds may be formulated as tablets or lozenges in conventional manner; and for rectal administration compositions such as suppositories or retention enemas, for example containing conventional suppository bases such as coca butter or other glyceride, can be used.

The compounds are preferably administered orally, for example in amounts of 0.5 to 300 μg/kg body weight, 1 to 4 times daily. For parenteral administration, the compounds may be administered in amounts of 0.01 to 10 μg/kg body weight, 1 to 4 times daily. The precise dose will of course depend on the age and condition of the patient.

Suitable methods for preparing the compounds of the invention are described below, the various groups and symbols being as defined above except where otherwise indicated.

(a) Compounds of formula (1) may be prepared by deprotection of a compound of formula (2)

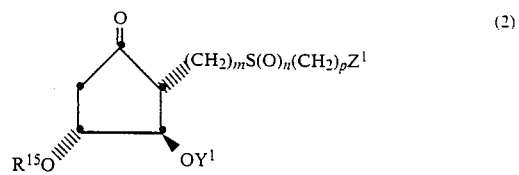

in which $Y^1$ is defined as a group

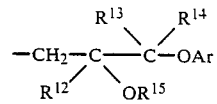

and $Z^1$ is Z as defined for formula (1) or is a group —$CH_2OR^{15}$ and $R^{15}$ is a suitable hydroxyl protecting group [e.g. tetrahydropyran-2-yl, tetrahydrofuran-2-yl, ethoxyethyl tri(hydrocarbyl)silyl or arylmethyl]

The $R^{15}$ groups in the compounds of formula (2) are conveniently the same, but they may be different if desired.

When $R^{15}$ is tri(hydrocarbyl)silyl the hydrocarbyl substituents may be the same or different e.g. $C_{1-6}$ alkyl, $C_{2-6}$ alkenyl, $C_{3-7}$ cycloalkyl, $C_{7-20}$ aralkyl and $C_{6-20}$ aryl groups. Such groups include methyl, ethyl, n-propyl, isopropyl, n-butyl, isobutyl, t-butyl, allyl, phenyl and benzyl. Preferred hydrocarbyl groups are $C_{1-4}$ alkyl, e.g. methyl and t-butyl. Trimethylsilyl and t-butyldimethylsilyl groups are particularly preferred.

When $R^{15}$ is an arylmethyl group it may contain up to 20 carbon atoms, e.g. benzyl, diphenylmethyl or triphenylmethyl.

The method used to deprotect the protected hydroxyl group depends on the nature of $R^{15}$ but in general acid hydrolysis or reduction may be used.

Thus, for example when $R^{15}$ is a tetrahydropyran-2-yl, tetrahydrofuran-2-yl or ethoxyethyl group deprotection may be carried out with an acid. Suitable acids include inorganic acids such as hydrochloric acid and organic acids such as acetic acid or trifluoroacetic acid. Suitable solvents include ethers (e.g. diethyl ether, dioxan and tetrahydrofuran), halogenated hydrocarbons (e.g. dichloromethane), hydrocarbons (e.g. toluene), dipolar aprotic solvents (e.g. acetone, acetonitrile, dimethylsulphoxide and dimethylformamide) and alcohols (e.g. methanol, ethanol and ethylene glycol). Where desired the solvents may be used in combination with water. The reaction may be carried out at any suitable temperature, such as from 0° to 50° C., e.g. 40° to 50° C.

A tri(hydrocarbyl)silyl group may for example be removed by acid hydrolysis, e.g. with dilute mineral acid or trifluoro acetic acid or by treatment with fluoride ion (e.g. from a quaternary ammonium fluoride such as tetra-n-butyl ammonium fluoride), or by treatment with aqueous hydrogen fluoride. Arylmethyl groups may be removed by reduction, e.g. by hydrogenolysis, e.g. with a noble metal catalyst such as platinum or palladium, or treatment with a Lewis acid (e.g. boron trifluoride-etherate) in the presence of a thiol (e.g. ethanethiol) in a suitable solvent such as dichloromethane at e.g. room temperature.

Compounds of formula (2) may be prepared by oxidation of a compound of formula (3)

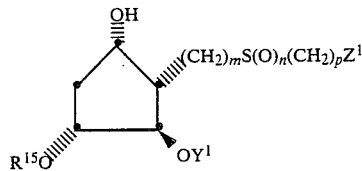

(3)

(where $Y^1$, $Z^1$ and $R^{15}$ are as defined just above) with for example dimethylsulphoxide, activated by N,N'-dicyclohexylcarbodiimide, in the presence of pyridinium trifluoroacetate in a solvent such as dichloromethane at e.g. $-10°$ C. to room temperature. Other conventional oxidative methods can also be used, for example pyridinium chlorochromate, pyridinium dichromate or Jones reagent.

In this reaction the $Z^1$ group is other than —CHO. When $Z^1$ is —CH$_2$OH, the —OH group will need to be protected in this reaction and may be for example a group —CH$_2$OR$^{15}$ described above.

It will be appreciated that the deprotection method (a) is usually applied in connection with the formation by oxidation of the cyclopentyl ring oxo group. Thus, the compounds of formula (1) may generally be prepared by oxidising a corresponding compound of formula (3) and the protecting groups removed thereafter.

The formation of the ring oxo group may however be effected prior to the introduction of the desired Z group by method (b), (c), (f) or (g) below and the protecting group(s) removed thereafter.

Compounds of formula (2) in which $Z^1$ is —CHO may be prepared by oxidising a corresponding compound in which $Z^1$ is —CH$_2$OH using for example an activated sulphur reagent e.g. a N-chlorosuccinimidedimethylsulphide complex in a suitable solvent (e.g. toluene or dichloromethane) at temperatures of for example $-25°$ to $+25°$ C. or pyridine-SO$_3$ complex in dimethylsulphoxide, preferably at 0° C. to room temperature.

Intermediates of formula (3) in which n is zero may be prepared by reaction of sulphonates of formula (4)

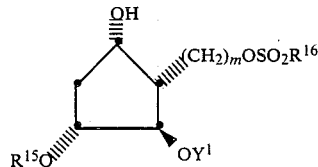

(4)

(in which $R^{15}$ and $Y^1$ are as defined above and $R^{16}$ is $C_{1-3}$ alkyl or aryl, e.g. monocyclic aryl such as 4-methylphenyl) with a thiol HS(CH$_2$)$_p$Z$^1$ or salts thereof (e.g. the sodium salt). The alkylation is preferably effected in the presence of base for example sodium hydride or potassium tert-butoxide in a solvent such as dimethylformamide at a suitable temperature (e.g. 0° C. to room temperature).

The thiols HS(CH$_2$)$_p$Z$^1$ are known compounds or may be prepared using methods analogous to those used for the preparation of the known compounds.

Intermediates of formula (4) may be prepared by reacting a corresponding diol of formula (5)

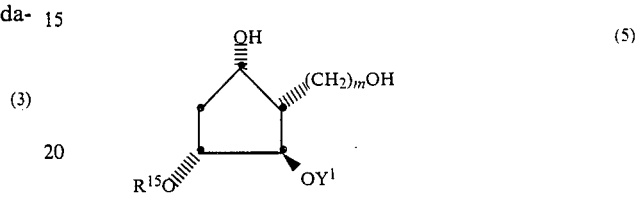

(5)

(in which $Y^1$ and $R^{15}$ are as defined above) with a sulphonyl halide, for example a sulphonyl chloride, $R^{16}SO_2Cl$ (where $R^{16}$ is as defined above). The sulphonylation is preferably effected in the presence of a suitable acid scavenger for example an organic base such as pyridine which can also be used as solvent. The reaction is preferably carried out at 0° C.

Although compounds of formula (4) can be isolated and purified they can also be prepared in situ and used immediately.

Compounds of formula (3) in which $Z^1$ is —CO$_2$H may also be prepared by hydrolysing a corresponding ester (e.g. a C$_{1-6}$ alkyl ester) e.g. using a base such as sodium hydroxide or potassium hydroxide in a suitable solvent (e.g. methanol) at room temperature to 50° C.

Intermediate diols of formula (5) may be prepared as shown in the following sequences:

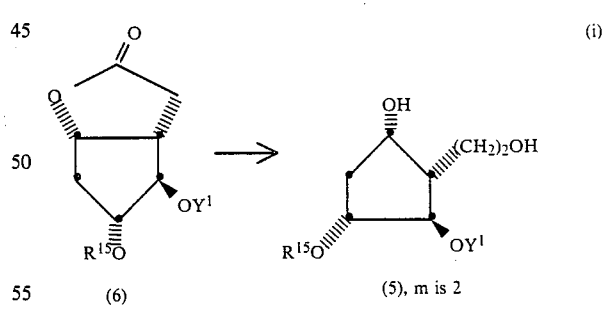

(6)      (5), m is 2

(i)

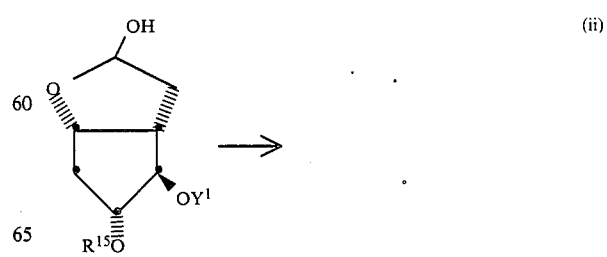

(7)

(ii)

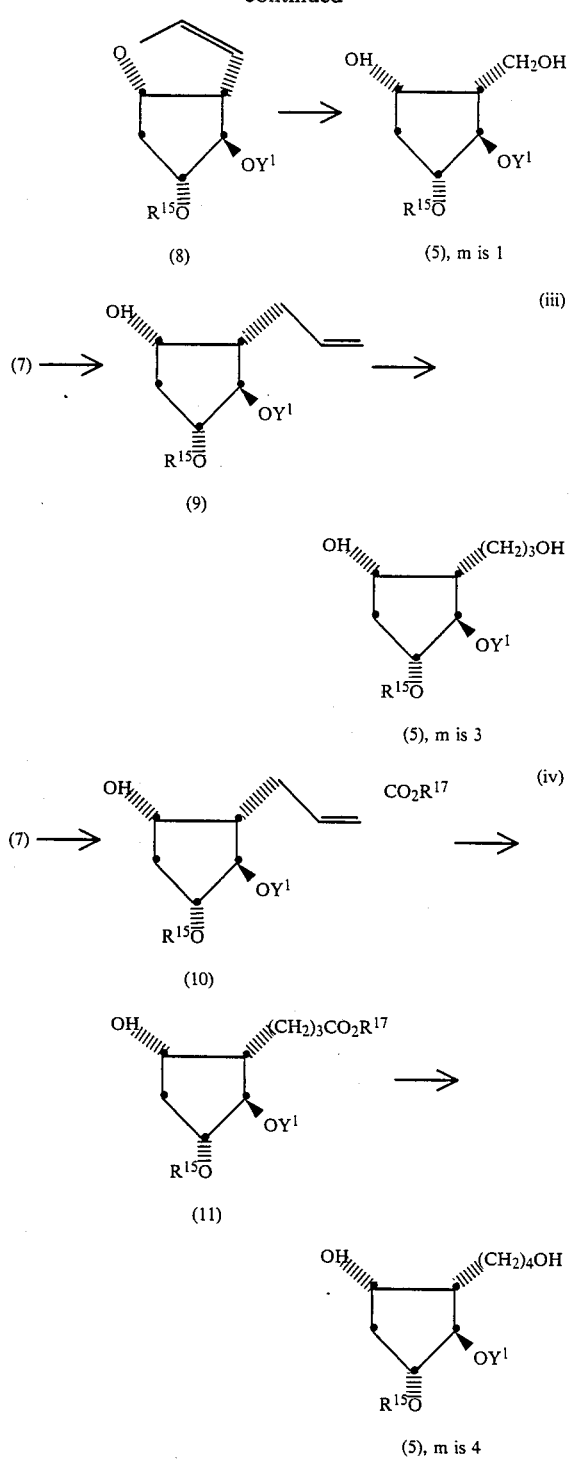

ture (e.g. −78° C.), followed by an in situ reduction with for example sodium borohydride. The enol ethers of formula (8) may be prepared from a lactol of formula (7) by reaction with a sulphonyl chloride $R^{16}SO_2Cl$ in the presence of a base (e.g. triethylamine or pyridine) in a suitable solvent (e.g. dichloromethane) at an appropriate temperature (e.g. −78° C. to room temperature).

In sequence (iii), diols of formula (5) in which m is 3 may be prepared by treating an olefin of formula (9) with diborane and reacting the resulting intermediate with alkaline hydrogen peroxide. The reaction can be carried out in a suitable solvent (e.g. tetrahydrofuran) at a suitable temperature (e.g. 0° C. to room temperature). Olefins of formula (9) may be prepared by reacting a lactol of formula (7) with an appropriate Wittig reagent $(R^{18})_3P=CH_2$ (where $R^{18}$ is aryl e.g. monocyclic aryl such as phenyl). Suitable solvents include tetrahydrofuran and dimethylsulphoxide. The reaction may be carried out at any suitable temperature from −70° to 50° C., preferably at room temperature.

In sequence (iv), diols of formula (5) in which m is 4 may be prepared by reduction of an ester of formula (11) by methods similar to those described above for the conversion of lactones of formula (6) into diols of formula (5) where m is 2. Esters of formula (11) can be prepared by reduction of the corresponding $\alpha,\beta$-unsaturated esters of formula (10) e.g. by hydrogenation in the presence of a noble metal catalyst such as platinum or palladium, in a suitable solvent e.g. an alcohol (e.g. ethanol). The unsaturated esters of formula (10) may be prepared by reaction of lactols of formula (7) with an appropriate Wittig reagent $(R^{18})_3P=CHCO_2R^{17}$ (where $R^{17}$ is $C_{1-3}$ alkyl or $C_{7-10}$ phenalkyl and $R^{18}$ is as defined above) in a suitable solvent for example ethanol, in the presence of an organic acid (e.g. acetic acid).

Lactones of formula (6) and lactols of formula (7) may be prepared by the methods described in European Patent Specification No. 160495.

(b) Compounds of formula (1) in which Z is $-CO_2R^1$ where $R^1$ is a group of type (a) or (b) may also be prepared by esterifying the corresponding compound in which Z is $-CO_2H$.

Such compounds may be prepared by conversion of the corresponding carboxylic acid into an activated derivative (e.g. a corresponding mixed anhydride) formed for example by reaction with an alkyl chloroformate (e.g. isobutyl chloroformate) or an acid chloride (e.g. pivaloyl chloride) in the presence of a suitable base (e.g. triethylamine or pyridine). The activated derivative can then be reacted with an appropriate alcohol, $R^1OH$, for example using a solvent such as dipolar aprotic solvent (e.g. acetone, acetonitrile or dimethylformamide) or a halogenated hydrocarbon (e.g. dichloromethane) at any suitable temperature (e.g. from −10° C. to room temperature).

In addition, such compounds in which $R^1$ is a $C_{1-6}$ alkyl group may be prepared by esterification of the corresponding carboxylic acid with a diazoalkane e.g. diazomethane, in a suitable solvent (e.g. dichloromethane or ether) at room temperature.

(c) Compounds of formula (1) in which Z is $-CONHR^9$ may also be prepared by amidation of the parent carboxylic acids or alkyl esters of formula (1), i.e. the corresponding compounds of formula (1) in which Z is $-CO_2R^1$ (where $R^1$ is a hydrogen atom or a $C_{1-6}$ alkyl group).

Thus, in sequence (i) diols of formula (5) in which m is 2 may be prepared by reduction of lactones of formula (6) with for example lithium aluminium hydride, sodium bis(2-methoxyethoxy)aluminium hydride or diisobutylaluminium hydride in a suitable solvent (e.g. tetrahydrofuran) at a suitable temperature (e.g. 0° C. to room temperature).

In sequence (ii) diols of formula (5) in which m is 1 may be prepared by ozonolysis of an enol ether of formula (8) in a suitable solvent (e.g. an ethanol-dichloromethane mixture) at an appropriate tempera- Conventional methods for converting acids and esters into amides may be used. For example, a reactive derivative of the carboxylic acid may be treated with a compound $R^9NH_2$ in a suitable solvent, e.g. acetone or acetonitrile. The reactive derivative is conveniently a mixed anhydride of the acid, formed for example by treatment of the acid with a chloroformate in the presence of a suitable base, e.g. triethylamine or pyridine. The chloroformate may for example be a $C_{1-6}$ alkyl (e.g. isobutyl), aryl (e.g. phenyl) or aralkyl (e.g. benzyl) chloroformate. Alternatively, the reactive derivative may be an imidazolide, formed for example by treatment of the acid with 1,1'-carbonyldiimidazole.

The ring hydroxy group may need to be in a protected form during these reactions. Conventional methods of protection and deprotection may be used, as described above in process (a).

(d) Compounds of formula (1) in which n is 1 may also be prepared by oxidation of compounds of formula (1) in which n is zero with a suitable oxidising agent, such as sodium periodate in a suitable solvent (e.g. methanol).

(e) Compounds of formula (1) in which n is 2 may also be prepared by oxidation of compounds of formula (1) in which n is zero or 1 with a suitable oxidising agent, such as a peracid (e.g. meta-chloroperoxybenzoic acid) in a suitable solvent (e.g. dichloromethane).

(f) Compounds of formula (1) in which Z is —$CO_2H$ may also be prepared by hydrolysis of a corresponding ester. The ester is desirably a labile ester, for example a compound of formula (1) in which Z is —$CO_2R^1$ where $R^1$ is tetrahydropyran-2-yl or tri(hydrocarbyl)silyl. Hydrolysis may be effected with an acid (e.g. acetic acid or trifluoroacetic acid) in a suitable solvent (e.g. aqueous tetrahydrofuran or dichloromethane) at an appropriate temperature.

(g) Compounds of formula (1) in which Z is —$CO_2R^1$ where $R^1$ is a group of type (c) may also be prepared by alkylation of the corresponding compound in which Z is —$CO_2H$ with a ketone of formula (12)

$$XCH_2COR^5 \qquad (12)$$

[in which X is a leaving group such as halogen (e.g. bromine)]. The reaction is preferably carried out in the presence of a base such as diisopropylethylamine or potassium fluoride in a solvent such as acetonitrile or dimethylformamide at a suitable temperature (e.g. room temperature).

Ketones of formula (12) are known compounds or may be prepared by methods analogous to those used for the preparation of the known compounds.

(h) Where salts of compounds of formula (1) are desired such salts may be formed by conventional methods e.g. by treating an acid of formula (1) with a base (e.g. an amine such as piperazine) in a solvent such as ether.

Complexes (e.g. cyclodextrin complexes) may be prepared using conventional methods e.g. by treating a compound of formula (1) with α, β-, γ-cyclodextrin in a suitable solvent.

The processes in methods (b)–(g) may also be applied to compounds of formula (2) and in particular to compounds of formula (3) and the products subsequently converted into compounds of formula (1) by the methods described above.

When a specific enantiomer of formula (1) is required, starting materials having the desired stereochemical configuration should be used in the above processes.

Such starting materials may be prepared for example using the methods described in European Patent Specification No. 160495 from an enantiomeric intermediate as described in European Patent Specification No. 74856.

The following examples illustrate the invention. Temperatures are in °C. 'Dried' refers to drying with anhydrous $MgSO_4$. T.l.c.—Thin layer chromatography on silica. Chromatography was carried out on silica gel.

The following abbreviations are used: ER-ether; EA-ethyl acetate; PE-petroleum ether (b.p. 40°–60° unless otherwise stated); THF-tetrahydrofuran; $CH_2Cl_2$-dichloromethane; $CHBr_3$-bromoform; DMSO-diemthylsulphoxide; MeOH-methanol; EtOH-ethanol; $Et_3N$-triethylamine; $LiAlH_4$-lithium aluminium hydride; HCl-hydrochloric acid; $NaHCO_3$-sodium bicarbonate; NaOH-sodium hydroxide; $CHCl_3$-chloroform.

Intermediate 1

[3aR-[3aα, 4α(2R*), 5β, 6aα]]-(+)-Hexahydro-4-[3-phenoxy-2-[(tetrahydro-2H-pyran-2-yl)oxy]propoxy]-5-[(tetrahydro-2H-pyran-2-yl)oxy]-2H-cyclopenta[b]furan-2-one

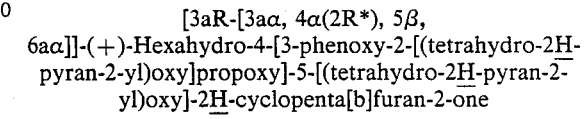

Intermediate 2

[3aR-[3aα, 4α(2R*), 5β,6aα]]-Hexahydro-4-[3-phenoxy-2-[(tetrahydro-2H-pyran-2-yl)oxy]propoxy]-5-[(tetrahydro-2H-pyran-2-yl)oxy]-2H-cyclopenta[b]furan-2-ol

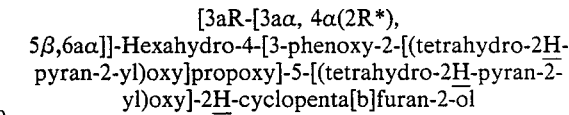

Intermediates 1 and 2 were prepared as described in European Patent Specification No. 160495.

Intermediate 3

[1S-[1α, 2β(2S*), 3α, 5α]]-5-Hydroxy-2-[3-phenoxy-2-[(tetrahydro-2H-pyran-2-yl)oxy]propoxy]-3-[(tetrahydro-2H-pyran-2-yl)cyclopentanethanol

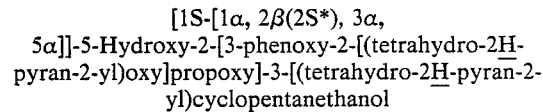

A solution of Intermediate 1 (1 g) in THF (20 ml) was added to a cooled, stirred mixture of $LiAlH_4$ (0.08 g) in THF (5 ml) under nitrogen. After 3 h, further $LiAlH_4$ (0.08 g) was added. After 2 h, water (2 ml) was added dropwise, the mixture was stirred for 10 min. and then partitioned between ER (50 ml) and 2N HCl (50 ml). The separated organic phase was washed with 8% $NaHCO_3$ solution (50 ml) and brine and aqueous washings back-extracted with ER (50 ml). The organic phases were dried and evaporated. The residue was purified by chromatography using EA→EA-MeOH (97:3 ) as eluant to give the *title compound* as an oil (0.79 g). I.r. ($CHBr_3$) 3600 and 3420 cm$^{-1}$.

Intermediate 4

[1S-[1α, 2β(2S*), 3α, 5α]]-Methyl 4-[[2-[5-hydroxy-2-[3-phenoxy-2-[(tetrahydro-2H-pyran-2-yl)oxy]propoxy]-3-[(tetrahydro-2H-pyran-2-yl)oxy]cyclopentyl]ethyl]thio]butanoate

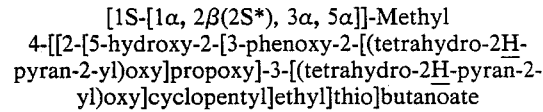

4-Methylbenzenesulphonyl chloride (0.36 g) and Intermediate 3 (0.69 g) were dissolved in dry pyridine (6 ml) at 0° under nitrogen. After 6 h, a solution of γ-thiobutyrolactone (0.6 ml) and sodium methoxide (0.27 g) in MeOH (7 ml), which had been pre-stirred under nitrogen for 1 h, was added. After 18 h at 0° the reaction mixture was allowed to warm to room temperature. After a further 7 h, ER (40 ml was added and the solution washed with 2N HCl (2×50 ml), 8% aqueous $NaHCO_3$ (50 ml) and saturated brine (50 ml). The washings were back-extracted with ER and the combined organic layers dried. Solvent evaporation and purification by chromatography using ER-PE (9:1) as eluant gave the *title compound* as an oil (0.39 g). I.r. (CHBr₃) 3580, 3510, 1725 cm⁻¹.

Intermediate 5

[3aR-[3aα, 4α(2R*), 5β, 6aα]]-4,5,6,6a-Tetrahydro-4-[3-phenoxy-2-[(tetrahydro-2H-pyran-2-yl)oxy]propoxy]-5-[(tetrahydro-2H-pyran-2-yl)oxy]-3-aH-cyclopenta[b]furan Methanesulphonyl chloride (1.0 ml) was added to a stirred solution of Intermediate 2 (4.62 g) in pyridine (30 ml). After 18 h the solution was cooled to −30° and water (0.4 ml) was added. The solution was allowed to warm to room temperature and after 20 min., partitioned between ether (200 ml) and 2N NaOH solution (200 ml), saturated brine (200 ml), dried and then evaporated. The residue was purified by chromatography using ER as eluant to give the *title compound* as an oil (0.66 g). T.l.c. (PE-ER, 3:2) Rf 0.24.

Intermediate 6

[1S-[1α, 2β(2S*), 3α, 5α]]-5-Hydroxy-2-[3-phenoxy-2-[(tetrahydro-2H-pyran-2-yl)oxy]propoxy]-3-[(tetrahydro-2H-pyran-2-yl)oxy]cyclopentanemethanol Ozone was bubbled through a solution of Intermediate 5 (0.71 g) in CH₂Cl₂ (30 ml) and EtOH (12 ml) containing Sudan III (0.5 mg) at −78°. When the solution decolourised it was purged with nitrogen for 30 min and then sodium borohydride (0.34 g) was added. After 10 min. at −78°, 30 min. at 0° and 1 h at room temperature, saturated ammonium chloride solution (50 ml) was added. The mixture was extracted with CH₂Cl₂ (2×50 ml) and the organic phases dried and evaporated. Purification of the residue by chromatography using EA-MeOH (98.5:1.5 →96:4) as eluant gave the *title compound* as an oil (0.63 g). I.r. (Neat) 3400 cm⁻¹.

Intermediate 7

[1S-[1α, 2β, 3β(2S*), 4α]]-(+)-3-[3-Phenoxy-2-[(tetrahydro-2H-pyran-2-yl)oxy]propoxy]-2-(2-propenyl)-4-[(tetrahydro-2H-pyran-2-yl)oxy]cyclopentanol Potassium t-butoxide (1.40 g) and (methyl)triphenylphosphonium bromide (4.50 g) were stirred in THF (50 ml) for 20 min. under nitrogen. A solution of Intermediate 2 (2.09 g) in THF (25 ml) was added and after stirring at room temperature for 18 h, saturated ammonium chloride solution (100 ml) was added. Extraction with ER (2×100 ml), drying, solvent evaporation and purification by chromatography using ER-PE (3:1) as eluant gave the *title compound* as an oil (1.98 g). I.r. (CHBr₃) 3590, 3530 cm⁻¹. [α]$_D^{20}$+23.8° (CHCl₃).

Intermediate 8

[1S-[1α, 2β(2S*), 3α, 5α]]-(+)-5-Hydroxy-2-[3-phenoxy-2-[(tetrahydro-2H-pyran-2-yl)oxy]propoxy]-3-[(tetrahydro-2H-pyran-2-yl)oxy]cyclopentane propanol A solution of borane (1.0M is THF, b 4.0 ml) was added to a solution of Intermediate 7 (1.93 g) in THF (30 ml) at 0° under nitrogen. After 4 h further borane solution (5.0 ml) was added. After a further 2 h water (5 ml) was added, followed by 2N NaOH (4.5 ml) and 30% aqueous hydrogen peroxide (3.4 ml). After 30 min. 20% aqueous sodium suphite (50 ml) was added and after stirring for a further 30 min., the mixture was extracted with ER (2×60 ml), the organic phases dried and then evaporated. Purification of the residue by chromatography using EA→EA-MeOH (93:3) as eluant gave the *title compound* as an oil (1.84 g). I.r. (CHBr₃) 3600, 3520 cm⁻¹. [α]$_D^{20}$+9.5° (MeOH).

Intermediate 9

[1S-[1α, 2β(2S*), 3α, 5α]]-Ethyl 4-[5-hydroxy-2-[3-phenoxy-2-[(tetrahydro-2H-pyran-2-yl)oxy]propoxy]-3-[(tetrahydro-2H-pyran-2-yl)oxy]cyclopentyl]-2-butenoate. E:Z, 60:40

(Carbethoxymethylene)triphenylphosphorane (1.05 g) was added to a stirred solution of Intermediate 2 (1.10 g) in EtOH (40 ml) containing one drop of acetic acid. After 5 days further (carbethoxymethylene)triphenylphosphorane (0.5 g) was added. After a further 2 days solvent was evaporated and the residue partitioned between EA (40 ml) and 8% aqueous NaHCO₃ (40 ml). The organic layer was washed with saturated brine (40 ml) and the aqueous layers back-extracted with EA (40 ml). The combined organic layers were dried, solvent was evaporated and the residue purified by chromatography using ER-PE (9:1) as eluant to give the *title compound* as an oil (1.14 g). I.r. (CHBr₃) 3520, 1705 cm−1.

Intermediate 10

[1S-[1α, 2β(2S*), 3α, 5α]]-(+)-Ethyl 4-[5-hydroxy-2-[3-phenoxy-2-[(tetrahydro-2H-pyran-2-yl)oxy]propoxy]-3-[(tetrahydro-2H-pyran-2-yl)oxy]cyclopentyl]butanoate A suspension of 10% palladium oxide on charcoal (0.28 g) in a solution of Intermediate 9 (1.08 g) in EA (50 ml) was stirred under an atmosphere of hydrogen for 2 h. Filtration and solvent evaporation gave the *title compound* as an oil (1.06 g). I.r. (CHBr₃) 3590, 3520, 1720 cm−1. [α]$_D^{20}$+23.2° (CHCl₃).

Intermediate 11

[1S-[1α, 2β(2S*), 3α, 5α]]-(+)-5-Hydroxy-2-[3-phenoxy-2-[(tetrahydro-2H-pyran-2-yl)oxy]propoxy]-3-[(tetrahydro-2H-pyran-2-yl)oxy]cyclopentanebutanol Sodium bis(2-methoxyethoxy)aluminium hydride (3.4M in toluene, 1.0 ml) was added to a solution of Intermediate 10 (1.02 g) in THF (20 ml) at 0°. After 1 h saturated ammonium chloride (25 ml) was added and the mixture extracted with EA (2×40 ml). Drying and solvent evaporation gave a residue which was purified by chromatography using EA as eluant to give *title compound* as an oil (0.78 g). I.r. (CHBr₃) 3600, 3520 cm−1. [α]$_D^{20}$+26° (CHCl₃).

Intermediate 12

(12a) [1S-[1α, 2β(2S*), 3α,5α]]-5-Hydroxy-2-[3-phenoxy-2-[(tetrahydro-2H-pyran-2-yl)oxy]propoxy]-3-[(tetrahydro-2H-pyran-2-yl)oxy]cyclopentaneethanol 4-methylbenzenesulphonate 4-Methylbenzenesulphonyl chloride (0.47 g) and Intermediate 3 (0.9 g) were dissolved in pyridine (10 ml) at 0° and the solution stirred for 8 h to give the *title compound*. T.l.c. (ER-PE, 5:1) Rf 0.35.

(12b) [1S-[1α, 2β(2S*), 3α, 5α]]-5-Hydroxy-2-[3-phenoxy-2-[(tetrahydro-2H-pyran-2-yl)oxy]propoxy]-3-[(tetrahydro-2H-pyran-2-yl)oxy]cyclopentanemethanol 4-methylbenzenesulphonate A solution of Intermediate 6 (0.29 g) and 4-methylbenzenesulphonyl chloride (0.15 g) in pyridine (3 ml) was kept at 4° for 24 h. ER (40 ml) was added and the solution washed with 2N HCl (40 ml), 8% aqueous $NaHCO_3$ (40 ml) and saturated brine (40 ml). The washings were back-extracted with ER (30 ml), the combined organic layers dried, and the solvent evaporated. The residue was purified by chromatography using ER-PE (9:1) as eluant to give the *title compound* as an oil (0.28 g). I.r. ($CHBr_3$) 3580, 3520, 1360 cm$^{-1}$.

The following compounds were prepared in a similar manner:

(12c) [1S-[1α, 2β(2S*), 3α, 5α]]-5-Hydroxy-2-[3-phenoxy-2-[(tetrahydro-2H-pyran-2-yl)oxy]propoxy]-3-[(tetrahydro-2H-pyran-2-yl)oxy]cyclopentanepropanol 4-methylbenzenesulphonate. I.r. ($CHBr_3$) 3520, 1352 cm$^{-1}$.

From Intermediate 8.

(12d) [1S-[1α, 2β(2S*), 3α, 5α]]-(+)-5-Hydroxy-2-[3-phenoxy-2-[(tetrahydro-2H-pyran-2-yl)oxy]propoxy]-3-[(tetrahydro-2H-pyran-2-yl)oxy]cyclopentanebutanol 4-methylbenzenesulphonate. I.r. ($CHBr_3$) 3600, 3530, 1355 cm$^{-1}$. $[\alpha]_D^{20}$ +21° ($CHCl_3$).

From Intermediate 11.

Intermediate 13

(13a) [1S-[1α, 2β(2S*), 3α, 5α]]-Methyl 3-[[2-[5-hydroxy-2-[3-phenoxy-2-[(tetrahydro-2H-pyran-2-yl)oxy]propoxy]-3-[(tetrahydro-2H-pyran-2-yl)oxy]cyclopentyl]ethyl]thio]propionate A solution of methyl 3-mercaptopropionate (1.1 ml) and potassium tert-butoxide (1.0 g) in dimethylformamide (15 ml) which had been prestirred for 1 h was added to a solution of freshly prepared Intermediate 12a in pyridine (10 ml) at 0°. After 17 h at 0° ER (100 ml) was added and the solution was washed with 2N HCl (100 ml), 8% aqueous $NaHCO_3$ (100 ml), water (100 ml) and saturated brine (100 ml). The washings were back-extracted with ER (100 ml) and the combined organic layers dried. Evaporation in the presence of $Et_3N$ (1 ml) gave a residue which was purified by chromatography using ER-PE (9:1) as eluant to give the *title compound* as an oil (0.45 g). T.l.c. (ER-PE, 9:1) Rf 0.25.

(13b) [1S[1α, 2β(2S*), 3α, 5α]]-Methyl 5-[[[5-hydroxy-2-[3-phenoxy-2-[(tetrahydro-2H-pyran-2-yl)oxy]propoxy]-3-[(tetrahydro-2H-pyran-2-yl)oxy]cyclopentyl]methyl]thio]pentanoate Sodium methoxide (0.22 g) was added to a stirred solution of methyl 5-(acetylthio)pentanoate (0.8 g) in dry MeOH (6 ml) under nitrogen. After 3 h the solvent was evaporated, the solid residue dissolved in dimethylformamide (5 ml) and a solution of the Intermediate 12b (0.26 g) in dimethylformamide (5 ml) was added. After stirring at room temperature for 3 days, ER (70 ml) was added and the solution washed with 2N HCl (70 ml), water (3×70 ml) and saturated brine (70 ml). The aqueous washings were back-extracted with ER (70 ml) and the combined organic layers dried. Solvent evaporation and purification by chromatography using ER-PE (9:1) as eluant gave the *title compound* as an oil (0.2 g). I.r. ($CHBr_3$) 3490, 3430, 1731 cm$^{-1}$.

The following compounds were prepared in a similar manner:

(13c) [1S-[1α, 2β(2S*), 3α, 5α]]-Methyl [[3-[5-hydroxy-2-[3-phenoxy-2-[(tetrahydro-2H-pyran-2-yl)oxy]propoxy]-3-[(tetrahydro-2H-pyran-2-yl)oxy]cyclopentyl]propyl]thio]acetate. I.r. ($CHBr_3$) 3520, 1728 cm$^{-1}$.

From Intermediate 12c and methyl mercaptoacetate.

(13d) [1S-[1α, 2β(2S*), 3α, 5α]]-Methyl 3-[[3-[5-hydroxy-2-[3-phenoxy-2-[(tetrahydro-2H-pyran-2-yl)oxy]propoxy]-3-[(tetrahydro-2H-pyran-2-yl)oxy]cyclopentyl]propyl]thio]propionate. T.l.c. (ER) Rf 0.34.

From Intermediate 12c and methyl 3-mercaptopropionate.

(13e) [1S-[1α, 2β(2S*), 3α, 5α]]-(+) Methyl [[4-[5-hydroxy-2-[3-phenoxy-2-[(tetrahydro-2H-pyran-2-yl)oxy]propoxy]-3-[(tetrahydro-2H-pyran-2-yl)oxy]cyclopentyl]butyl]thio]acetate. I.r. ($CHBr_3$) 3520, 1728 cm$^{-1}$. $[\alpha]_D^{20}$ +25.6 ($CHCl_3$).

From Intermediate 12d and methyl mercaptoacetate.

Intermediate 14

[1S-[1α, 2β(2S*), 3α, 5α]]-4-[[2-[5-Hydroxy-2-[3-phenoxy-2-[(tetrahydro-2H-pyran-2-yl)oxy]propoxy]-3-[(tetrahydro-2H-pyran-2-yl)oxy]cyclopentyl]ethyl]thio]butanoic acid 5N NaOH (3 ml) was added to a solution of Intermediate 4 (0.6 g) in MeOH (14 ml). After 2 h the mixture was poured into water (100 ml) and washed with ER (100 ml). The aqueous extract was acidified with ammonium chloride (80 ml) and extracted with EA (3×75 ml). The combined organic extracts were dried and evaporated to leave the *title compound* as an oil (0.6 g). I.r. ($CHBr_3$) 3500, 3400–2500, 1728 cm$^{-1}$.

Intermediate 15

(15a) [1S-[1α, 2β(2S*), 3α, 5α]]-4-(Benzoylamino)phenyl 4-[[2-[5-hydroxy-2-[3-phenoxy-2-[(tetrahydro-2H-pyran-2-yl)oxy]propoxy]-3-[(tetrahydro-2H-pyran-2-yl)oxy]cyclopentyl]ethyl]thio]butanoate Pivaloyl chloride (0.15 ml) was added to a solution of Intermediate 14 (0.6 g) and $Et_3N$ (0.5 ml) in dry dimethylformamide (5 ml) at 0°. After 15 min a solution of 4-(benzoylamino)phenol (0.53 g) in dimethylformamide (2 ml) was added and stirring continued for 6 h at 0° and 18 h at room temperature. The reaction mixture was diluted with EA (100 ml) and washed with water (2×60 ml) and brine (50 ml). The aqueous washings were back-extracted with EA (100 ml) and the combined organic phases dried and evaporated. Purification by chromatography on $Et_3N$-deactivated silica gel using cyclohexane-EA (2:1) as eluant gave the *title compound* as a gum (0.35 g). I.r. ($CHBr_3$) 3520, 3420, 1748, 1728, 1672 cm$^{-1}$.

The following compound was prepared in a similar manner:

(15b) [1S-[1α, 2β(2S*), 3α, 5α]]-Methyl 4-[4-[[2-[5-hydroxy-2-[3-phenoxy-2-[(tetrahydro-b 2H-pyran-2-yl)oxy]propoxy]-3-[(tetrahydro-2H-pyran-2-yl)oxy]cyclopentyl]ethyl]thio]-1-oxobutoxy]benzoate. I.r. ($CHBr_3$) 3520, 1754, 1715 cm$^{-1}$.

From Intermediate 14 and 4-hydroxybenzoic acid methylester.

Intermediate 16

(16a) [1R-[1α, 2β(2S*), 3α]]-4-(Benzoylamino)phenyl [4-[[2-[5-oxo-2-[3-phenoxy-2-[(tetrahydro-2H-pyran-2-yl)oxy]propoxy]-3-[(tetrahydro-2H-pyran-2-yl)oxy]cyclopentyl]ethyl]thio]butanoate A stirred solution of Intermediate 15a (0.33 g) in dry $CH_2Cl_2$ (10 ml) and dry DMSO (0.85 ml) was treated with dicyclohexylcarbodiimide (0.53 g) followed by pyridinium trifluoroacetate (0.33 g). After 22 h water (5 ml) was added and after 5 min the mixture filtered through 'hyflo' and evaporated. The residue was dissolved in ER (20 ml) and washed consecutively with water (10 ml), 10% copper sulphate solution (20 ml) and brine (20 ml). The aqueous washings were back-extracted with ER (20 ml) and the combined extracts dried and evaporated. Purification by chromatography on acid-washed (pH 3.8) silica using cyclohexane:EA (2:1) as eluant gave the *title compound* as an oil (0.25 g). I.r. ($CHBr_3$) 3420, 1738, 1670 $cm^{-1}$.

The following compounds were prepared in a similar manner:

(16b) [1R-[1α, 2β(2R*), 3α]]-Methyl 4-[1-oxo-4-[[2-[5-oxo-2-[3-phenoxy-2-[(tetrahydro-2H-pyran-2-yl)oxy]propoxy]-3-[(tetrahydro-2H-pyran-2-yl)oxy]cyclopentyl]ethyl]thio]butoxy]benzoate. I.r. ($CHBr_3$) 1740, 1717 $cm^{-1}$.

From Intermediate 15b.

(16c) [1R-[1α, 2β(2R*), 3α]]-Methyl 4-[[2-[5-oxo-2-[3-phenoxy-2-[(tetrahydro-2H-pyran-2yl)oxy]propoxy]-3-[(tetrahydro-2H-pyran-2yl)oxy]cyclopentyl]ethyl]thio]butanoate. T.l.c. (ER-PE, 2:1) Rf 0.28.

From Intermediate 4.

(16d) [1R-[1α, 2β(2R*), 3α]]-Methyl 4-[[2-[5-oxo-2-[3-phenoxy-2-[(tetrahydro-2H-pyran-2-yl)oxy]propoxy]-3-[(tetrahydro-2H-pyran-2-yl)oxy]cyclopentyl]ethyl]sulfinyl]butanoate. I.r. ($CHBr_3$) 1738 $cm^{-1}$.

From Intermediate 17a.

The following compounds were similarly prepared except that purification by chromatography was effected using 2:1 ER-PE→ER as eluant.

(16e) [1R-[1α, 2β(2R*), 3α]]-Methyl 3-[[2-[5-oxo-2-[3-phenoxy-2-[(tetrahydro-2H-pyran-2-yl)oxy]propoxy]-3-[(tetrahydro-2H-pyran-2-yl)oxy]cyclopentyl]ethyl]thio]propionate as an oil (0.09 g). T.l.c. (ER-PE, 2:1) Rf 0.24.

From Intermediate 13a (0.44 g).

(16f) [1R-[1α, 2β(2R*), 3α]]-Methyl 5-[[[5-oxo-2-[3-phenoxy-2-[(tetrahydro-2H-pyran-2-yl)oxy]propoxy]-3-[(tetrahydro-2H-pyran-2-yl)oxy]cyclopentyl]methyl]thio]pentanoate. I.r. ($CHBr_3$) 1740 $cm^{-1}$.

From Intermediate 13b.

(16g) [1R-[1α, 2β(2R*), 3α]]-Methyl [[3-[5-oxo-2-[3-phenoxy-2-[(tetrahydro-2H-pyran-2-yl)oxy]propoxy]-3-[(tetrahydro-2H-pyran-2-yl)oxy]cyclopentyl]propyl]thio]acetate. I.r. ($CHBr_3$) 1735 $cm^{-1}$.

From Intermediate 13c.

(16h) [1R-[1α, 2β(2R*), 3α]]-Methyl 3-[[3-[5-oxo-2-[3-phenoxy-2-[(tetrahydro-2H-pyran-2-yl)oxy]propoxy]-3-[(tetrahydro-2H-pyran-2-yl)-oxy]cyclopentyl]propyl]thio]propionate. I.r. ($CHBr_3$) 1735 $cm^{-1}$.

From Intermediate 13d.

(16i) [1R-[1α, 2β(2R*), 3α]]-(−)-Methyl [[4-[5-oxo-2-[3-phenoxy-2-[(tetrahydro-2H-pyran-2-yl)oxy]propoxy]-3-[(tetrahydro-2H-pyran-2-yl)-oxy]cyclopentyl]butyl]thio]acetate. I.r. ($CHBr_3$) 1736 $cm^{-1}$. $[α]_D^{20}$ −15.3° ($CHCl_3$).

From Intermediate 13e.

(16j) [1R-[1α, 2β(2R*), 3α]]-Methyl [[4-[5-oxo-2-[3-phenoxy-2-[(tetrahydro-2H-pyran-2-yl)oxy]propoxy]-3-[(tetrahydro-2H-pyran-2-yl)-oxy]cyclopentyl]butyl]sulfinyl]acetate. I.r. ($CHBr_3$) 1732 $cm^{-1}$.

From Intermediate 17b.

(16k) [1R-[1α, 2β(2R*), 3α]]-Methyl [[4-[5-oxo-2-[3-phenoxy-2-[(tetrahydro-2H-pyran-2-yl)oxy]propoxy]-3-[(tetrahydro-2H-pyran-2-yl)oxy]cyclopentyl]butyl]sulfonyl]acetate. I.r. ($CHBr_3$) 1740 $cm^{-1}$.

From Intermediate 17c.

Intermediate 17

(17a) [1S-[1α, 2β(2S*), 3α, 5α]]-Methyl 4-[[2-[5-hydroxy-2-[3-phenoxy-2-[(tetrahydro-2H-pyran-2-yl)oxy]propoxy]-3-[(tetrahydro-2H-pyran-2-yl)oxy]cyclopentyl]ethyl]sulfinyl]butanoate A solution of sodium periodate (0.25 g) in water (5 ml) was added to a stirred solution of Intermediate 4 (0.22 g) in MeOH (10 ml). After 18 h EA (50 ml) was added and the solution washed with half-saturated brine (40 ml) and saturated brine (40 ml). The washings were back-extracted with EA (40 ml) and the combined organic layers dried. Evaporation and purification by chromatography using EA-MeOH (92:8→85:15) as eluant gave the *title compound* as an oil (0.18 g). I.r. ($CHBr_3$) 3520, 1730 $cm^{-1}$.

The following compound was prepared in a similar manner except that purification by chromatography was effected using EA-MeOH (16:1) as eluant:

(17b) [1S-[1α, 2β(2S*), 3α, 5α]]-(+)-Methyl [[4-[5-hydroxy-2-[3-phenoxy-2-[(tetrahydro-2H-pyran-2-yl)oxy]propoxy]-3-[(tetrahydro-2H-pyran-2-yl)oxy]cyclopentyl]butyl]sulfinyl]acetate as an oil (0.39 g). I.r. ($CHBr_3$) 3520, 1733 $cm^{-1}$. $[α]_D^{20}$ +24° ($CHCl_3$).

From Intermediate 13e (0.39 g).

(17c) [1S-[1α, 2β(2S*), 3α, 5α]]-Methyl [[4-[5-hydroxy-2-[3-phenoxy-2-[(tetrahydro-2H-pyran-2-yl)oxy]propoxy]-3-[(tetrahydro-2H-pyran-2-yl)oxy]-cyclopentyl]butyl]sulfonyl]acetate $NaHCO_3$ (0.2 g) and meta-chloroperbenzoic acid (80–90% pure, 0.07 g) were added to a stirred of Intermediate 17b (0.2 g) in $CH_2Cl_2$ (5 ml) at 0°. After 1 h the solution was allowed to warm slowly to room temperature and, after a further hour, further meta-chloroperbenzoic acid (5 mg) was added. After a further 2 h ER (40 ml) was added and the solution washed with 8% aqueous $NaHCO_3$ (40 ml) and saturated brine (40 ml). The aqueous washings were back-extracted with ER (40 ml) and the combined organic layers dried. Solvent evaporation gave the *title compound* as an oil (0.19 g). I.r. ($CHBr_3$), 3590, 3520, 1740 $cm^{-1}$.

EXAMPLE 1

[1R-[1α, 2β(R*), 3α]]4-(Benzoylamino)phenyl 4-[[2-[3-hydroxy-2-(2-hydroxy-3-phenoxypropoxy)-5-oxocyclopentyl]ethyl]thio]butanoate A solution of Intermediate 16a (0.24 g) in acetic acid-water-THF (20:10:3, 7 ml) was heated at 40° for 4.5 h. The solvent was removed in vacuo and the residue purified by chromatography on acid-washed (pH 3.8) silica using EA-cyclohexane (3:1) as eluant to give the *title compound* as a white solid (0.09 g), m.p. 103°–5°.

Analysis Found: C, 65.28; H, 5.98; N, 2.18. $C_{33}H_{37}NO_8S$ requires C, 65.22; H, 6.14; N, 2.30%.

The following compounds were prepared in a similar manner.

EXAMPLE 2

[1R-[1α, 2β(R*), 3α]]-Methyl 4-[[4-[2-[3-hydroxy-2-(2-hydroxy-3-phenoxypropoxy)-5-oxocyclopentyl]ethyl]thio]-1-oxobutoxy]benzoate as an oil (0.12 g). I.r. (CHBr$_3$) 3580, 3440, 1745, 1718 cm$^{-1}$.

Analysis Found: C, 61.64; H, 6.28. $C_{28}H_{34}O_9S$ requires: C, 61.6; H, 6.23%.

From Intermediate 16b (0.3 g) except that toluene-acetonitrile (2:1) was used as eluant.

EXAMPLE 3

[1R-[1α, 2β(R*), 3α]]-(−)-Methyl 4-[[2-[3-hydroxy-2-(2-hydroxy-3-phenoxypropoxy)-5-oxocyclopentyl]ethyl]thio]butanoate as an oil (0.2 g). I.r. (CHBr$_3$) 3580, 3450, 1738 cm$^{-1}$. [α]$_D^{20}$ −36.0° (CHCl$_3$).

Analysis Found: C, 58.87; H, 7.19. $C_{21}H_{30}O_7S$ requires C, 59.13; H, 7.09%.

From Intermediate 16c (0.4 g) except that ER-MeOH (97:3) was used as eluant.

EXAMPLE 4

[1R-[1α, 2β(R*), 3α]]-Methyl 4-[[2-[3-hydroxy-2-(2-hydroxy-3-phenoxypropoxy)-5-oxocyclopentyl]ethyl]thio]sulfinyl]butanoate as an oil (0.066 g). T.l.c. (EA-MeOH, 9:1) Rf 0.29. I.r. (CHBr$_3$) 3580, 1736 cm$^{-1}$.

From Intermediate 16d (0.12 g) except that EA-MeOH (9:1) was used as eluant.

EXAMPLE 5

[1R-[1α, 2β(R*), 3α]]-Methyl 3-[[2-[3-hydroxy-2-(2-hydroxy-3-phenoxypropoxy)-5-oxocyclopentyl]ethyl]thio]propionate as an oil (0.03 g). T.l.c. (ER-MeOH, 97:3) Rf 0.23. I.r. (CHBr$_3$) 3580, 3440, 1735 cm$^{-1}$.

From Intermediate 16e (0.09 g) except that ER-MeOH (97:3) was used as eluant.

EXAMPLE 6

[1R-[1α, 2β(R*), 3α]]-Methyl 5-[[[3-hydroxy-2-(2-hydroxy-3-phenoxypropoxy)-5-oxocyclopentyl]methyl]thio]pentanoate as an oil (0.036 g).

I.r. (CHBr$_3$) 3580, 3450, 1740 cm$^{-1}$.

Analysis Found: C, 59.06; H, 7.16. $C_{21}H_{30}O_7S$ requires C, 59.13; H, 7.09%.

From Intermediate 16f (0.12 g) except that ER-MeOH (97:3) was used as eluant.

EXAMPLE 7

[1R-[1α, 2β(R*), 3α]]-Methyl [[3-[3-hydroxy-2-(2-hydroxy-3-phenoxypropoxy)-5-oxocyclopentyl]propyl]thio]acetate as an oil (0.077 g). I.r. (CHBr$_3$) 3580, 3440, 1737 cm$^{-1}$.

Analysis Found: C, 58.58; H, 7.15. $C_{20}H_{28}O_7S$ requires C, 58.23; H, 6.84%.

From Intermediate 16g (0.18 g) except that ER-MeOH (97:3) was used as eluant.

EXAMPLE 8

[1R-[1α, 2β(R*), 3α]]-Methyl 3-[[3-[3-hydroxy-2-(2-hydroxy-3-phenoxypropoxy)-5-oxocyclopentyl]propyl]thio]propionate as an oil (0.04 g). T.l.c. (ER-MeOH, 97:3) Rf 0.27. I.r. (CHBr$_3$) 3580, 3440, 1738, 1734 cm$^{-1}$.

From Intermediate 16h (0.093 g) except that ER-MeOH (97:3) was used as eluant.

EXAMPLE 9

[1R-[1α, 2β(R*), 3α]]-(−)-Methyl [[4-[3-hydroxy-2-(2-hydroxy-3-phenoxypropoxy)-5-oxocyclopentyl]butyl]thio]acetate as an oil (0.1 g). I.r. (CHBr$_3$) 3590, 3450, 1740 cm$^{-1}$. [α]$_D^{20}$ −40.6° (CHCl$_3$).

Analysis Found: C, 58.98; H, 7.33. $C_{21}H_{30}O_7S$ requires C, 59.13; H, 7.09%.

From Intermediate 16i (0.2 g) except that ER-MeOH (97:3) was used as eluant.

EXAMPLE 10

[1R-[1α, 2β(R*), 3α]]-Methyl [[4-[3-hydroxy-2-(2-hydroxy-3-phenoxypropoxy)-5-oxocyclopentyl]butyl]sulfinyl]acetate as an oil (0.068 g). I.r. (CHBr$_3$) 3590, 1740 cm$^{-1}$.

Analysis Found: C, 57.12; H, 7.09. $C_{21}H_{30}O_8S$ requires C, 57.00; H, 6.83%.

From Intermediate 16j (0.12 g) except that ER-MeOH (97:3) was used as eluant.

EXAMPLE 11

[1R-[1α, 2β(R*), 3α]]-Methyl [[4-[3-hydroxy-2-(2-hydroxy-3-phenoxypropoxy)-5-oxocyclopentyl]butyl]sulfonyl]acetate as an oil (0.084 g). T.l.c. (ER-MeOH, 97:3) Rf 0.27. I.r. (CHBr$_3$) 3590, 3450, 1742 cm$^{-1}$.

From Intermediate 16k (0.14 g) except that ER-MeOH (97:3) was used as eluant.

The following are examples of pharmaceutical formulations using compounds of the invention. In the examples, the term "active ingredient" is used to denote a compound of the invention, such as a compound described in the preceding examples.

1. Tablets

These may be prepared by direct compression

|  | mg/tablet |
|---|---|
| Active Ingredient | 0.015 to 0.2 |
| Magnesium stearate, BP | 1.5 |
| Microcrystalline cellulose, USP to compression weight | 150.0 |

The active ingredient is blended with about 10% of the microcrystalline cellulose then blended with the remaining microcrystalline cellulose and magnesium stearate. The blend is then compressed using 6 mm diameter punches into tablets on a suitable machine.

The tablets may be film coated with suitable film forming materials e.g. methyl cellulose or hydroxypropyl methylcellulose using standard techniques.

2. Capsules

|  | mg/tablet |
|---|---|
| Active ingredient | 0.015 to 0.2 |
| Magnesium stearate, BP | 1.0 |
| *Starch 1500 to fill weight | 100.0 |

*A form of directly compressible starch.

The active ingredient is preblended with some of the Starch 1500 then this preblend is mixed with the remaining Starch 1500 and magnesium stearate. The mix is

We claim:

1. Compounds of the general formula (1)

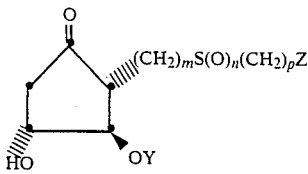

wherein
m is 1 to 4
n is zero, 1 or 2;
p is 1 to 4;
Z is a group —CO$_2$R$^1$ where R$^1$ is
   (a) a hydrogen atom or a C$_{1-6}$ alkyl, C$_{7-10}$ phenalkyl or 2-naphthyl group;
   (b) phenyl or phenyl substituted by C$_{1-4}$ alkyl, C$_{1-4}$ alkoxy, C$_{1-4}$ alkanoyl, methylthio, methylsulphinyl, methylsulphonyl, halogen, —CO$_2$R$^2$ (where R$^2$ is a hydrogen atom or C$_{1-4}$ alkyl or phenyl), —NHCOR$^2$ (where R$^2$ is as defined above or is a phenyl group or a phenyl group substituted by hydroxyl, CH$_3$CONH— or

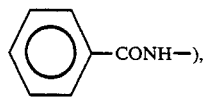

—CONR$^3$R$^4$ (where R$^3$ and R$^4$ may be the same or different and are each a hydrogen atom or a C$_{1-4}$ alkyl group), —NHCONH$_2$, —CH$_2$CH(CONH$_2$)NHCOCH$_3$ or

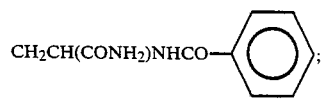

(c) a group —CH$_2$COR$^5$ where R$^5$ is phenyl or phenyl substituted by C$_{1-4}$ alkyl, C$_{1-4}$ alkoxy, C$_{1-4}$ alkanoyl, methylthio, methylsulphinyl, methylsulphonyl, halogen, —CO$_2$R$^6$ (where R$^6$ is a hydrogen atom or C$_{1-4}$ alkyl or phenyl), —CONR$^7$R$^8$ (where R$^7$ and R$^8$ may be the same or different and are each a hydrogen atom or a C$_{1-4}$ alkyl group), —NHCOR$^6$ (where R$^6$ is as defined above, or is a phenyl group or a phenyl group substituted by hydroxyl, CH$_3$CONH— or

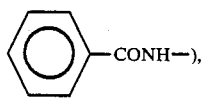

—NHCONH$_2$, —CH$_2$CH(CONH$_2$)NHCOCH$_3$ or

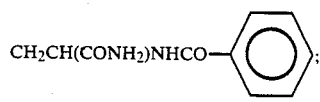

or R$^5$ is 2-naphthyl; or Z is —CH$_2$OH, —CHO, or CONHR$^9$ where R$^9$ is a hydrogen atom or C$_{1-4}$ alkyl, aryl, —COR$^{10}$ (where R$^{10}$ is a hydrogen atom or a C$_{1-4}$ alkyl or aryl group) or —SO$_2$R$^{11}$ (where R$^{11}$ is a C$_{1-4}$ alkyl or aryl group);

Y is

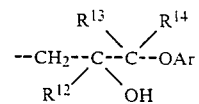

where R$^{12}$, R$^{13}$ and R$^{14}$ are each a hydrogen atom or a methyl and at least one is a hydrogen atom, and Ar is a phenyl group or phenyl substituted by one or two C$_{1-4}$ alkyl, C$_{1-4}$ alkoxy, C$_{1-4}$ alkylthio, C$_{1-4}$ alkylsulphinyl, C$_{1-4}$ alkylsulphonyl, halogen or trifluoromethyl groups; and the physiologically acceptable salts, solvates and complexes thereof.

2. Compounds as claimed in claim 1 in which Z is a group —COOR$^1$ where R$^1$ is:
   (a) a hydrogen atom, C$_{1-3}$ alkyl or 2-naphthyl group;
   (b) phenyl substituted by a methoxy, acetyl, —CO$_2$CH$_3$, —NHCOCH$_3$, benzoylamino, —CONH$_2$, —CON(CH$_3$)$_2$ or —CH$_2$CH(CONH$_2$)NHCOCH$_3$ group;
   (c) —CH$_2$COR$^5$ where R$^5$ is phenyl group substituted by a methoxy, acetyl, —CO$_2$CH$_3$, —NHCOCH$_3$, benzoylamino, —CONH$_2$, —CON(CH$_3$)$_2$ or —CH$_2$CH(CONH$_2$)NHCOCH$_3$ group, or R$^5$ is a 2-naphthyl group; or Z is —CH$_2$OH, —CHO, —CONH$_2$, —CONHCH$_3$, —CONHCOCH$_3$, —CONHSO$_2$CH$_3$ or

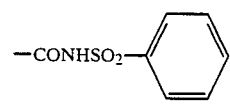

3. Compounds as claimed in claim 1 in which n is 0.

4. Compounds as claimed in claim 1 in which R$^{13}$ and R$^{14}$ are hydrogen atoms and Ar is phenyl or phenyl substituted by chloro or fluoro.

5. Compounds as claimed in claim 1 in which:
n is zero
m is 3 or 4 and p is 1 or
m is 2 or 3 and p is 2 or
m is 1 and p is 4 or
m is 2 and p is 3;
Z is a group CO$_2$R$^1$ [where R$^1$ is a hydrogen atom or C$_{1-3}$ alkyl, 2-naphthyl or phenyl substituted by methoxy, acetyl, —CO$_2$CH$_3$, —NHCOCH$_3$, benzoylamino, —CONH$_2$, —CON(CH$_3$)$_2$ or —CH$_2$CH(CONH$_2$)NHCOCH$_3$];
R$^{12}$ is a hydrogen atom or methyl;
R$^{13}$ and R$^{14}$ are hydrogen atoms;
Ar is phenyl or phenyl substituted by fluoro or chloro; and the physiologically acceptable salts, solvates and complexes thereof.

6. Compounds as claimed in claim 5 in which Z is a group —CO$_2$R$^1$ where R$^1$ is a hydrogen atom, methyl or phenyl substituted in the para-position by —CO$_2$CH$_3$ or benzoylamino.

7. Compounds as claimed in claim 1 in which the carbom atom carrying the —(CH$_2$)$_m$S(O)$_n$(CH$_2$)$_p$Z group is in the R-configuration.

8. Compounds as claimed in claim 1, said compounds being: [1R-[1α, 2β(R*), 3α]]-4-(benzoylamino)phenyl 4-[[2-[3-hydroxy-2-(2-hydroxy-3-phenoxypropoxy)-5-oxocyclopentyl]ethyl]thio]butanoate; [1R-[1α, 2β(R*), 3α]]-methyl 4-[[[2-[3-hydroxy-2-(2-hydroxy-3-phenoxypropoxy)-5-oxocyclopentyl]ethyl]thio]-1-oxobutyl]oxy]benzoate; and [1R-[1α, 2β(R*), 3α]]-(−)methyl 4-[[2-[3-hydroxy-2-(2-hydroxy-3-phenoxypropoxy)-5-oxocyclopentyl]ethyl]thio]butanoate; and complexes thereof.

9. A pharmaceutical composition comprising a compound as claimed in claim 1 together with one or more pharmaceutical carriers.

10. A process for the preparation of a compound as claimed in claim 1 which comprises:

(a) deprotecting a compound of formula (2)

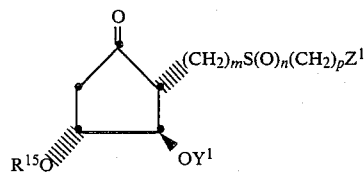

(2)

in which $Y^1$ is a group

and $Z^1$ is Z as defined for formula (1) or is a group $-CH_2OR^{15}$ and $R^{15}$ is a hydroxyl protecting group;

(b) in the preparation of a compound in which Z is $-CO_2R^1$ where $R^1$ is a group of type (a) or (b), esterifying the corresponding compound in which Z is $-CO_2H$;

(c) in the preparation of a compound in which Z is $-CONHR^9$, amidating a corresponding compound of formula (1) in which Z is $-CO_2R^1$ (where $R^1$ is a hydrogen atom or a $C_{1-6}$ alkyl group);

(d) in the preparation of a compound in which n is 1, oxidising a corresponding compound in which n is 0;

(e) in the preparation of a compound in which n is 2, oxidising a corresponding compound in which n is 0 or 1;

(f) in the preparation of a compound in which Z is $-CO_2H$, hydrolysing a corresponding ester;

(g) in the preparation of a compound in which Z is $-CO_2R^1$ where $R^1$ is a group of type (c), alkylating the corresponding compound in which Z is $-CO_2H$ with a ketone of formula (12)

$$XCH_2COR^5 \qquad (12)$$

in which X is a leaving group; or (h) treating an acid of formula (1) with a base to form a salt or treating a compound of formula (1) with cyclodextrin to form a complex.

* * * * *